(12) United States Patent
Thyne (10) Patent No.: US 10,465,106 B2
(45) Date of Patent: Nov. 5, 2019

(54) OPTIMIZED SALINITY FOR ENHANCED WATER FLOOD APPLICATIONS

(71) Applicant: ESal, LLC, Laramie, WY (US)

(72) Inventor: Geoffrey Thyne, Laramie, WY (US)

(73) Assignee: ESal, LLC, Laramie, WY (US)

(*) Notice: Subject to any disclaimer, the term of this patent is extended or adjusted under 35 U.S.C. 154(b) by 92 days.

(21) Appl. No.: 15/948,551

(22) Filed: Apr. 9, 2018

(65) Prior Publication Data

US 2018/0298270 A1    Oct. 18, 2018

Related U.S. Application Data

(63) Continuation of application No. 15/420,335, filed on Jan. 31, 2017, now Pat. No. 9,938,450, which is a continuation of application No. 14/479,899, filed on Sep. 8, 2014, now Pat. No. 9,581,007.

(60) Provisional application No. 61/888,875, filed on Oct. 9, 2013.

(51) Int. Cl.
| | |
|---|---|
| *E21B 43/20* | (2006.01) |
| *E21B 43/16* | (2006.01) |
| *E21B 47/00* | (2012.01) |
| *E21B 43/40* | (2006.01) |
| *C09K 8/588* | (2006.01) |
| *E21B 49/08* | (2006.01) |
| *G01N 33/18* | (2006.01) |
| *G01N 33/28* | (2006.01) |

(52) U.S. Cl.
CPC .............. *C09K 8/588* (2013.01); *E21B 43/20* (2013.01); *E21B 43/40* (2013.01); *E21B 49/08* (2013.01); *G01N 33/1846* (2013.01); *G01N 33/2823* (2013.01); *E21B 2049/085* (2013.01)

(58) Field of Classification Search
CPC .......... E21B 43/20; E21B 43/16; E21B 47/00; E21B 43/40
See application file for complete search history.

(56) References Cited

U.S. PATENT DOCUMENTS

| 7,255,166 B1 | 8/2007 | Weiss |
|---|---|---|
| 7,455,109 B2 | 11/2008 | Collins |

(Continued)

FOREIGN PATENT DOCUMENTS

| EP | 2179064 | 4/2012 |
|---|---|---|
| WO | 2010092095 | 8/2010 |

(Continued)

OTHER PUBLICATIONS

Brady et al., "Surface complexation modeling for waterflooding of sandstones," SPE Journal, 2013, vol. 18(2), pp. 214-218, Abstract, 3 pages. 2013.

(Continued)

*Primary Examiner* — Catherine Loikith
(74) *Attorney, Agent, or Firm* — Holzer Patel Drennan (57) ABSTRACT

Methods for enhanced oil recovery from subterranean formations by treating a produced water prior to injection into the subterranean hydrocarbon reservoir and manipulating produced water compositions to increase the rate and/or amount of oil that is recovered from producing wells and/or a hydrocarbon reservoir. The treatment of the produced water can increase the pH of the water from about 0.75 to about 2.0.

20 Claims, 2 Drawing Sheets

(56) References Cited

U.S. PATENT DOCUMENTS

| | | | |
|---|---|---|---|
| 7,549,472 B2* | 6/2009 | Morrow | C09K 8/52 166/263 |
| 8,188,012 B2 | 5/2012 | Weerasooriya | |
| 8,486,269 B2 | 7/2013 | McGuire | |
| 8,812,271 B1 | 8/2014 | Brady | |
| 9,518,449 B1 | 12/2016 | Brady | |
| 9,727,928 B2 | 8/2017 | Heneman | |
| 2010/0096129 A1 | 4/2010 | Hinkel | |
| 2011/0256085 A1 | 10/2011 | Talingting Pabalan | |
| 2011/0306525 A1 | 12/2011 | Lighthelm | |
| 2012/0067579 A1 | 3/2012 | Pich | |
| 2012/0125603 A1 | 5/2012 | Willingham | |
| 2012/0125605 A1 | 5/2012 | Willingham | |
| 2014/0262275 A1 | 9/2014 | Dean | |
| 2017/0356281 A1 | 12/2017 | Brady | |

FOREIGN PATENT DOCUMENTS

| | | |
|---|---|---|
| WO | 2014158906 | 10/2014 |
| WO | 2016105395 | 6/2016 |

OTHER PUBLICATIONS

Dubey et al., "Base No. and Welling Properties of Crude Oil," SPE Reservoir Engineering,1993, vol. 8(3), pp. 195-200, Abstract, 3 pages. 1993.

Chemical Verification of the EOR Mechanism by Using Low Saline/Smart Water in Sandstone Alireza RezaeiDoust, Tina Puntervold, and Tor Austad Energy & Fuels 2011 25 (5), 2151-2162, Mar. 31, 2011. 2011.

Anderson, William G. "Wettability Literature Survey Part 2: Wettability Measurement." Conoco, Inc. 1986. Journal of Petrolum Technology. 1986.

Abdallah, Wael et al. "Fundamentals of Wettability." Oilfield Review. 2007. 2007.

Anderson, William G. "Wettability Literature Survey Part 1: Rock/Oil/Brine Interactionas and the Effects of Core Handing on Wettability." Conoco, Inc. 1986. Journal of Petrolum Technology. 1986.

Brady, Patrick V. and Thyne, Geoffrey. "Functional Wettability in Carbonate Reservoirs" Energy & Fuels. ACS Publications. Oct. 11, 2016.

Brady, Patrick V. et al. "Altering wettability to recover more oil from tight formations." Journal of Unconventional Oil and Gas Resources 15. 79-83. 2016. Elsevier Ltd. 2016.

Brady, Patrick V. et al. "Surface Complexation Modeling for Improved Oil Recovery." SPE International. 14-18. Oil Recovery Symposium. Apr. 2012. Apr. 2012.

Buckley, J.S. and Liu, L. "Some mechanisms of crude oil/brine/solid interactions." Petroleum Recolery Research Center, NM Institute of Mining and Technology. Jan. 21, 1998.

Buckley, Jill S. "Effective wettability of minerals exposed to crude oil." Current Opinion in Colloid & Interface Science 6. 2001. 191-196. Elsevier. 2001.

Celik, M.S. and Somasundaran, P. "Effect of Pretreatments on Flotation and Electrokinetic Properties of Coal." Elsevier Scientific Publising Company. Colloids and Surfaces, 1 (1980) 121-124. 1980.

Drummond, Carlos and Israelachvili, Jacob. "Fundamental studies of crude oil—surface water interactions and its relationship to reservoir wettability." Journal of Petroleum Science and Engineering 45 (2004) 61-81. Elsevier. 2004.

Dubey, S.T. and Doe, P.H. "Base Number and Wetting Properties of Crude Oils." SPE Reservoir Engineering. Aug. 1993.

Erzuah, S. et al. "Wettability Characterization Using the Flotation Technique Coupled with Geochemical Simulation." The National IOR Centre of Norway. 19th European Symposium on Improved Oil Recovery. 24-27. EAGE. Apr. 2017.

Hirasakl, G.J. "Wettability: Fundamentals and Surface Forces." SPE Formulation Evaluation. Jun. 1991.

Kaszuba, John P. et al. "Supercritical carbon dioxide and sulfur in the Madison Limestone: A natural analog in southwest Wyoming for geologic carbon-sulfur co-sequestration." Earth and Planetary Science Letters 309 (2011) 131-140. Elsevier. 2011.

Mwangi, Paulina et al. "The effect of organic acids on wettability of sandstone and carbonate rocks." Journal of Petroleum Science and Engineering 165 (2018) 428-435. Elsevier. 2018.

Qiao, Chenghe. "Understanding the Chemical Mechanisms for Low Salinity Waterflooding." SPE Europec featured at 78th EAGE Conference and Exhibition. Jun. 22, 2016.

Mwangi, Paulina et al. "Extensive Experimental Wettability Study in Sandstone and Carbonate-Oil-Brine Systems: Part 1—Screening Tool Development." International Symposium of the Society of Core Analysts. Sep. 2013.

Skold, Mangus. "Using UCODE_2005 and PHREEQC to Determine Thermodynamic Constants from Experimental Data." Ground Water. vol. 45, No. 3. Jun. 2007.

Smith, J.T. and Ehrenberg, S.N. "Correlation of carbon dioxide abundance with temperature in clastic hydrocarbon reservoirs: relationship to inorganic chemical equilibrium." Marine and Petroleum Geology, 1989, vol. 6. May 1989.

Thyne, Geoffrey. "Wettability Alteration in Reservoirs: How it Applies to Alaskan Oil Production." Society of Petroleum Engineers. 2016.

Sohal, M. Adeel, et al. "Novel Application of the Flotation Technique to Measure the Wettability Changes by Ionically Modified Water for Improved Oil Recovery in Carbonates." ACS Publications. Energy & Fuels. 2016.

Fjelde, Ingebret et al. "Screeing of the Potential for Different Injection Water Compositions to Alter Wettability to More Water-Wet." Society of Petroleum Engineers. 2017.

Erzuah, Samuel et al. "Wettability Estimation by Surface Complexation Simulations." SPE Europec. EAGE Conference and Exhibition. Jun. 2017.

Thyne, Geoffrey. "A Review of the Measurement of Wettability." Science Based Solutions LLC. 2016.

Thyne, Geoffrey and Brady, Patrick. "Evaluation of formation water chemistry and scale prediction: Bakken Shale." Applied Geochemistry 75 (2016) 107-113. Elsevier. 2016.

Wu, Yongfu et al. "An Experimental Study of Wetting Behavior and Surfactant EOR in Carbonates With Model Compounds." SPE Journal. Mar. 2008.

Gamage et al., "Comparison of Oil Recovery by Low Salinity Waterflooding in Secondary and Tertiary Recovery Modes" SPE International. 2011.

Salathiel et al., "Oil Recovery by Surface Film Drainage in Mixed-Wettability Rocks," Journal of Petroleumm Technology. 1216-1224. Oct. 1973.

Thyne et al. "Evaluation of the Effect of Low Salinity Waterflooding for 26 Fields in Wyoming." SPE International. 2011.

* cited by examiner

OPTIMIZED SALINITY FOR ENHANCED WATER FLOOD APPLICATIONS

CROSS REFERENCE TO RELATED APPLICATIONS

This application is a continuation of U.S. application Ser. No. 14/479,899, filed on Sep. 8, 2014, which claims priority to and the benefit under 35 U.S.C. § 119(e) to U.S. Provisional Application Ser. No. 61/888,875, filed on Oct. 9, 2013. Each of these references are incorporated herein in their entirety by reference.

TECHNICAL FIELD

This invention relates to methods for enhanced oil recovery from subterranean formations. More particularly, it relates to methods for manipulating produced water compositions to increase the rate and/or amount of oil that is recovered from producing wells and/or a hydrocarbon reservoir.

BACKGROUND OF DISCLOSURE

Enhanced oil recovery refers to the process of producing liquid hydrocarbons by methods other than the conventional use of reservoir energy or water floods which utilize reservoir repressurizing schemes with injected water. On average, conventional production methods will produce from a reservoir about 30% of the initial oil in place. The remaining oil, nearly 70% of the initial resource, is a large and attractive target for enhanced oil recovery methods.

Waterflooding recovers oil by the water moving through the reservoir as a bank of fluid that displaces the oil ahead of it. The recovery efficiency of a waterflood is largely a function of the sweep efficiency of the flood and the ratio of the oil and water viscosities. Sweep efficiency is a measure of how well the water has come in contact with the available pore space in the oil-bearing zone. Gross heterogeneities in the rock matrix lead to low sweep efficiencies. Fractures, high-permeability streaks, and faults are examples of gross heterogeneities. Homogeneous rock formations provide the optimum setting for high sweep efficiencies.

The overall recovery efficiency of any fluid displacement process depends upon the macroscopic displacement efficiency and the microscopic displacement efficiency. The macroscopic displacement efficiency is a measure of how well the displacing fluid has come in contact with the oil-bearing parts of the reservoir. The microscopic displacement efficiency is a measure of how well the displacing fluid mobilizes the residual oil once the fluid has come in contact with the oil.

The microscopic displacement efficiency is affected by several factors, including interfacial and surface tension forces, wettability, capillary pressure, and relative permeability. The interfacial tension between two fluids represents the amount of work required to create a new unit of surface area at the interface. The interfacial tension can also be thought of as a measure of the immiscibility of two fluids. When certain chemical agents are added to an oil-brine system, it is possible to reduce the interfacial tension by several orders of magnitude, thereby greatly improving their miscibility.

The tendency for a solid to prefer one fluid over another is called wettability. Wettability is a function of the chemical composition of both the fluids and the rock. Rock surfaces can be either oil-wet or water-wet, depending on the chemical composition of the fluids. The degree to which a rock is either oil-wet or water-wet is strongly affected by the adsorption or desorption of constituents in the oil phase. Large, polar compounds in the oil phase can absorb onto solid surfaces leaving an oil film that may alter the wettability of the surface.

Chemical flooding relies on the addition of one or more chemical compounds to an injected fluid such as water, to either reduce the interfacial tension between the reservoir oil and the injected fluid, or to improve the displacement efficiency of the injected fluid. There are three general methods in chemical flooding technology. The first is polymer flooding, in which a large molecular weight component is used to increase the displacing fluid viscosity. This leads to improved displacement efficiencies in the reservoir. The second and third methods, micellar-polymer and alkaline flooding, make use of chemicals that reduce the interfacial tension between an oil and a displacing fluid.

The addition of large-molecular-weight molecules called polymers to an injected water may increase the effectiveness of a conventional waterflood. Polymers are sometimes added to the water in concentrations ranging from 250 to 2000 parts per million (ppm). A polymer solution is more viscous than a brine without polymer. In a flooding application, the increased viscosity may alter the mobility ratio between the injected fluid and the reservoir oil. The improved mobility ratio may lead to better displacement efficiencies and thus higher oil recoveries.

The micellar-polymer process uses a surfactant to lower the interfacial tension between the injected fluid and the reservoir oil. A surfactant migrates to the interface between the oil and water phases and helps make the two phases more miscible. Interfacial tensions can be reduced from ~30 dyne/cm, found in typical waterflooding applications, to 10-4 dyne/cm with the addition of as little as 0.1-5.0 wt % surfactant to water-oil systems. As the interfacial tension between an oil phase and a water phase is reduced, the capacity of the aqueous phase to displace the trapped oil phase from the pores of the rock matrix increases. The reduction of interfacial tension results in a shifting of the relative permeability curves such that the oil will flow more readily at lower oil saturations.

When an alkaline solution is mixed with certain crude oils, surfactant molecules are formed. When the formation of surfactant molecules occurs in situ, the interfacial tension between the brine and oil phases can be reduced. The reduction of interfacial tension causes the microscopic displacement efficiency to increase, which may increase oil recovery. Alkaline substances that have been effectively used include sodium hydroxide, sodium orthosilicate, sodium metasilicate, sodium carbonate, ammonia, and ammonium hydroxide.

However, enhanced oil recovery methods face numerous challenges. This is largely due to the complexity of an oil producing well. Factors that affect the impact of a waterflooding system start with the geography and type of rock formation and include the chemical composition of the formation (e.g. sandstone versus limestone), the heterogeneity of the formation, the porosity of the rock, and the formation's macroscopic features (e.g. presence of cracks, fissures and the like). The characteristics of the injection water itself are equally important. These include temperature, viscosity, pH, salinity and osmotic strength. The combined characteristics of the rock formation, the injection water, and the oil all define how the oil in the formation will interact and/or react with the injection water and thus define key metrics such as surface wettability, displacement efficiencies, viscous stripping, oil film flow, oil saturation and buoyancy forces. So, it is clear that enhancing oil recovery in existing production wells is an extremely complex process and no single injection water composition or waterflooding method is likely to be efficient and cost effective for every, or even most, rock formations treated.

Thus, there remains a significant need in the field of enhanced oil recovery for producing efficient and cost effective aqueous displacement injection compositions, and methods for applying said compositions to subterranean rock formations, wherein the compositions and methods are specifically designed for the specific rock formation being treated. There also remains a need for adaptive waterflooding methods, that to continue to maximize oil recovery during the dynamic changes that occur in any rock formation, waterflooding procedure.

SUMMARY OF DISCLOSURE

It is therefore an objective of this disclosure to provide improved enhanced oil recovery (EOR) methods for hydrocarbon reservoirs, and more specifically, producing wells, injection wells, or both, that provide increased oil recoveries and yields and, wherein the methods are tailored to meet the needs of the specific hydrocarbon reservoir being treated.

It is a further objective of this disclosure to provide adaptive enhanced oil recovery methods that utilize feedback methods to optimize the EOR method being used for a specific well, rock formation, and produced water, that accounts for the dynamic changes that occur in this system during the course of the waterflooding treatment process.

An aspect of the present invention relates to a method for increasing oil recovery from a subterranean hydrocarbon reservoir comprising recovering a produced water from a wellbore, analyzing the produced water to determine at least one production metric of the produced water, estimating at least one optimized metric, wherein the at least one optimized metric correlates with the at least one production metric, altering the produced water to produce a treated injection water, wherein the injection water is characterized by a metric that approximates the at least one optimized metric, and injecting the injection water into the hydrocarbon reservoir in one or more locations to increase the overall production of hydrocarbons from the reservoir. Altering the produced water may include diluting the produced water with another water supply, or it may include the addition of a material other than water. Examples of a material other than water include acids, bases and salts.

This Summary of the Invention is neither intended nor should it be construed as being representative of the full extent and scope of this disclosure. Moreover, references made herein to "the present disclosure" or aspects thereof, should be understood to mean certain embodiments and should not necessarily be construed as limiting all embodiments to a particular description. The present invention is set forth in various levels of detail in the Summary of the Invention as well as in the attached drawings and the Description of Embodiments and no limitation as to the scope is intended by either the inclusion or non-inclusion of elements, components, etc. in this Summary of the Invention. Additional aspects will become more readily apparent from the Description of Embodiments, particularly when taken together with the drawings.

BRIEF DESCRIPTION OF DRAWINGS

The accompanying drawings are incorporated into and form a part of the specification to illustrate examples of how the aspects, embodiments, or configurations can be made and used and are not to be construed as limiting the aspects, embodiments, or configurations to only the illustrated and described examples. Further features and advantages will become apparent from the following, more detailed, description of the various aspects, embodiments, or configurations.

The following is a component list and the associated numbering as shown in the attached figures.

| REFERENCE NUMERALS | |
|---|---|
| # | component |
| 100 | producing well |
| 110 | injection well |
| 120 | processing station |
| 130 | oil produced |
| 140 | alteration water |
| 150 | produced water containing oil |
| 160 | injection water |
| 170 | rock formation |
| 200 | separator |
| 210 | produced water |
| 220 | mixing station |
| 230 | control center |
| 240 | measurement device |
| 250 | control valve |

DETAILED DESCRIPTION OF EMBODIMENTS

The following detailed description illustrates the invention by way of example and not by way of limitation. This description will clearly enable one skilled in the art to make and use the invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

An aspect of the present invention relates to a method for increasing oil recovery from a subterranean hydrocarbon reservoir comprising recovering a produced water from a wellbore, analyzing the produced water to determine at least one production metric of the produced water, estimating at least one optimized metric, wherein the at least one optimized metric correlates with the at least one production metric, altering the produced water to produce an injection water, wherein the injection water is characterized by a metric that approximates the at least one optimized metric, and injecting the injection water into the hydrocarbon reservoir in one or more locations to increase the overall production of hydrocarbons from the reservoir.

In some embodiments of the present invention, the at least one production metric comprises at least one of a chemical composition metric, a physical property, a thermodynamic property, an equilibrium property, and combinations thereof. As used herein, a "chemical composition metric" refers to a concentration of at least one chemical compound or component. A concentration may be in terms of weight percent, mole percent, or other concentrations known to one skilled in the art. As used herein, a "physical property" refers to properties of solids, liquids, or gases, including but not limited to viscosity, surface tension, and thermal conductivity. As used herein, the term "equilibrium property" refers to a property that describes one or more equilibrium concentrations of components sharing a closed system; e.g. a subterranean rock formation with formation water. Examples of equilibrium properties include, but are not limited to, equilibrium constants, chemical potentials, and molar free energies. As used herein, a "thermodynamic property" refers to a property that describes the energy of a system. Examples of thermodynamic properties include, but are not limited to, enthalpy, entropy, fugacity, and heat capacity. In some further embodiments of the present invention, the at least one production metric is at least one of pH, salinity, osmotic strength, an ion concentration, and combinations thereof.

In some embodiments of the present invention, the analyzing step of the produced water may comprise quantitative measurements of the concentrations of sodium, potassium, calcium, magnesium, chloride, carbonate, and sulfate ions present in the produced water. In some embodiments of the present invention, these measurements may be made using at least one analytical method comprising inductively coupled plasma (ICP) spectrophotometry, atomic adsorption spectrophotometry, liquid chromatography, UV-VIS spectrophotometry, gas chromatography, specific ion measurements, titrimetric methods, colorimetric methods, and combinations thereof. In some further embodiments of the present invention, the produced water may be analyzed by determining the pH of the produced water. Any one of these analytical methods may provide the at least one production metric of the produced water.

In some further embodiments of the present invention, the analyzing step may include a correction step to adjust for a variety of dynamic changes that may occur in the well. Wells produce large volumes of formation water during oil production. The chemistry of the formation water is important to understand when drilling, completing and water flooding the reservoir. It is the combined chemistry of the formation water, the rock formation itself and the chemistry of the oil that determine the optimum composition of an injection water for maximizing oil recovery. However, drilling and drilling fluids often contaminate formation water samples making chemical analysis difficult. In addition, formation fluids undergo significant physio-chemical changes during production, primarily loss of dissolved gases and cooling so parameters such as pH and temperature that are measured at the surface are inaccurate. Therefore, analysis of the water produced from a well may not provide a satisfactory indication of the chemistry of the formation water, thus reducing the reliability of the subsequent estimating step for calculating an optimized injection water metric. A correction step may remedy or lessen the magnitude of this problem.

Thus, in some embodiments of the present invention, the analyzing step may include a correction step, whereby analysis of the production water provides a more reliable and accurate estimate of the reservoir's formation water chemical composition. In some embodiments of the present invention, the correction step may assume that solute concentrations for some components in the reservoir are controlled by water-rock equilibrium. Such components may include $SiO_2$, $HCO_3$, Fe, Al, Ca, Mg, Ba, and $SO_4$. It may be assumed that other components remain unchanged as a result of well activities. These may include Na, K, and Cl. Further examples of correction steps that may be taken to better estimate the formation water chemistry include adjusting pH measurements to account for changes due to the loss of dissolved carbon dioxide as the well pressure is decreased, and adjusting the precipitation of minerals like barite ($BaSO_4$) due to cooling of the produced water during production. Other correction steps may be taken using thermodynamic and equilibrium relationships known to one of ordinary skill in the art. In some embodiments of the present invention, the correction step of the analyzing step provides an estimate of the reservoir pH.

In some embodiments of the present invention, recovering a produced water for analysis may involve obtaining a small, continuous slip-stream taken from a main flow of produced water exiting a producing well. In-line analyzers may be placed in the slip-stream to obtain automated, or semi-automated analysis of the produced water. Alternatively, produced water may be sampled manually at a sample point (e.g. a valve) located in a main conduit that directs the produced water flow from the well. Analysis may then be provided in a batch fashion using instruments located remotely in an analytical lab.

In some further embodiments of the present invention, the analyzing step may further comprise analyzing a sample of the rock formation. Analysis of the rock formation may include, but is not limited to, identifying the presence and quantity of carbonate minerals, clays, and sulfates. In some further embodiments of the invention, analysis of the rock formation may comprise determining a carbonate composition in the range from about 2 wt % to about 20 wt %. In some further embodiments of the invention, analysis of the rock formation may comprise determining a clay composition in the range from about 2 wt % to about 20 wt %. In some further embodiments of the invention, analysis of the rock formation may comprise determining a sulfate composition in the range from about 0.5 wt % to about 5 wt %. In some further embodiments of the invention, analysis of the rock formation may comprise determining a carbonate composition in the range from about 2 wt % to about 20 wt %, a clay composition in the range from about 2 wt % to about 20 wt %, and a sulfate composition in the range from about 0.5 wt % to about 5 wt %. In some embodiments, a sulfate may comprise at least one of gypsum, anhydrite, and combinations thereof. Analytical methods for quantifying carbonate minerals may include acid digestion, geophysical logs, thin section point counting, well cutting descriptions, and X-ray diffraction analysis. Analytical methods for quantifying clays may include geophysical logs, thin section point counting, X-ray diffraction analysis, and sieve analysis.

In some embodiments of the present invention, the estimating step may provide at least one optimized metric that may comprise at least one of a target degree of dilution or increase in salinity, a target concentration of major ions, a target concentration of divalent ions, a target concentration of monovalent ions, a target pH, and combinations thereof, wherein the optimized metric, when applied to the produced water may create an injection water that may maximize or improve the release of oil from the subterranean rock formation into the injection water. In some further embodiments of the present invention, the estimating step may provide an optimized metric corresponding to a target degree of dilution or increase in salinity which may maximize or improve the release of oil from the subterranean rock formation into the injection water.

In some embodiments of the present invention, at least one optimized metric may be estimated in the estimating step by the use of a modified thermodynamic equilibrium model that includes specific chemical reactions between the mineral surfaces identified and the polarity of functional groups of the oil being recovered. The equilibrium constants for the thermodynamic equilibrium model may be derived from experimental data and an automatic parameter estimation computer code. The amount of incremental oil predicted to be recovered may be calculated using reservoir mineral abundance, as known to one skilled in the art. In some further embodiments of the present invention, a modified thermodynamic equilibrium model may be utilized that estimates the equilibrium constants between oil and mineral surfaces based on the at least one production metric attained from the analysis step. For enabling purposes, some of the equilibrium equations utilized are included in the Appendix.

In some embodiments of the present invention, the altering step may comprise at least one of treating the produced water, mixing the produced water with a second water, adding a second water containing at least one additive to the produced water, and combinations thereof, whereby the altering step creates an injection water characterized by a parameter that approximates the at least one optimized metric from the estimating step. In some further embodiments of the present invention, the altering step may comprise addition of a water to the produced water from at least one of an aquifer, a river, a stream, a lake, an ocean, a subsurface formation, and combinations thereof. In still further embodiments, the water added to the produced water may further comprise inorganic salts, whereby addition of the organic salts may change the relative proportions of monovalent and divalent ions. One skilled in the art will recognize that the optimum ratio of ions will depend upon the particular reservoir being treated, the type of rock formation, etc. In still further embodiments of the present invention, the altering step may comprise treating the produced water utilizing at least one of reverse osmosis, electrodialysis, water softening technology, water deionization technology, water distillation, and combinations thereof. The altering step may decrease or increase at least one metric of the produced water, including but not limited to pH, salinity, and a concentration.

Altering the produced water may include diluting the produced water with another water supply, or it may include the addition of a material other than water, or in addition to water. Examples of a material other than water that may be added to the produced water include acids, bases, salts, and combinations thereof.

In some embodiments of the present invention, the water added to the produced water to create an injection water may comprise at least one of a viscosifying agent, a density modifier, a pH adjustment agent, a salinity adjustment agent, a displacement agent, a dispersant, and combinations thereof. In some embodiments of the present invention, the water may comprise a least one viscosifying polymer agent. U.S. Patent Application Publication No. 2011/0256085 provides a list of exemplary viscosifying agents and is incorporated herein in its entirety for enabling purposes.

In some embodiments of the present invention, the water added to the produced water for creating an injection water may be metered directly into the produced water conduit from the well bore. A pump may be used to overcome the well head pressure. For embodiments that include at least one additive added to the water, for example a pH adjustment agent, the additive may be first mixed with the dilution water before the mixture is metered directly into the produced water conduit. Mixing of liquid additives with the produced water may be achieved using static mixers, continuous stirred tank reactors, or any other suitable mixing device. For embodiments that utilize solid additives, the solid additives may be added to the dilution water in either a batch or continuous stirred tank reactor. More than one batch reactor running in parallel may be optimum for cases were multiple solid additives are used, and wherein the time to completely dissolve these additives into the dilution water takes a significant amount of time; e.g. more than ten minutes. One batch reactor may then feed a treated water into the produced water conduit, while a second batch of treated water is being prepared.

In some embodiments of the present invention, the treated produced water may be injected into the subterranean hydrocarbon reservoir, wherein the treated produced water interacts with the subterranean hydrocarbon reservoir to produce an increase in the pH of the treated produced water at a mixing front from about 0.75 pH units to about 2.0 pH units, resulting in an improved overall hydrocarbon recovery. In some further embodiments, the increase in the pH of the treated produced water at the mixing front may be from about 1.0 pH unit to about 1.5 pH units.

In some embodiments of the present invention, the rock formation comprises at least one of sandstone, limestone, dolomite, chalk formations, and combinations thereof. In some further embodiments of the present invention, the rock formation comprises a carbonate material. In some further embodiments of the present invention, the rock formation comprises a sandstone. The chemistry, pH and dilution factor of the treated produced water is designed to ensure there is no formation damage or formation of precipitates in the reservoir during re-injection.

In some embodiments of the present invention, the enhanced oil recovery method comprising recovering a produced water from a well, analyzing the produced water, estimating at least one optimized metric, altering the produced water to produce an injection water that is characterized by a metric that approximates the at least one optimized metric, and injecting the injection water into the well, may be an iterative process. Treatment of a rock formation using waterflooding techniques is a dynamic process. For example, the injection water will mix with the formation water, salts may form in the produced water, scales may form on the rock surfaces, minerals on the rock surfaces may leach into the produced water. These and many other processes may continuously change the chemistries of the well waters, rock formation, and the oil being recovered. Therefore, the optimized metric and resultant injection water formed by altering the produced water with an alteration water, may only significantly improve oil recovery for a finite period of time due to dynamic chemistry changes in the system. Repeating the enhanced oil recovery steps of the present invention at least one time, may extend the time period, wherein meaningful gains in oil recovery are attained. In some embodiments of the present invention, the recovery steps of the present invention may be completed once, or twice or three times. In further embodiments of the present invention, the recovery steps may be repeated until the enhanced oil recovery falls below an acceptable recovery metric or economic metric.

Figure 1:
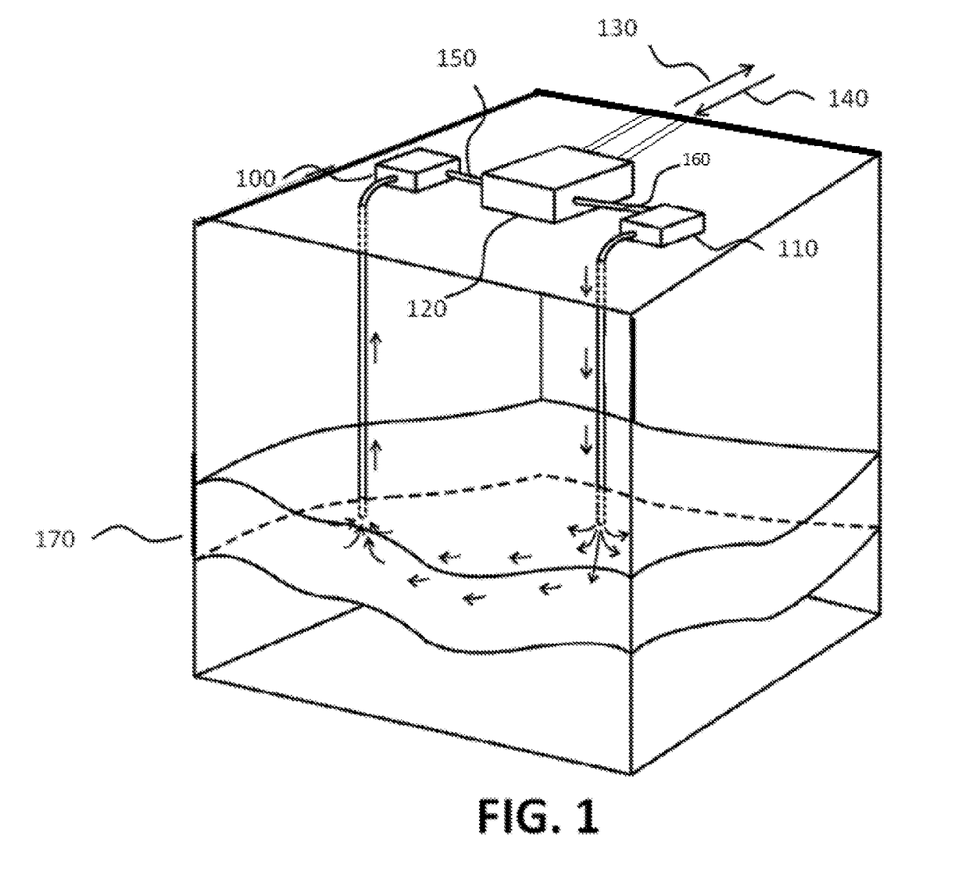
FIG. 1 shows one embodiment of the present invention, an enhanced oil recovery system comprising a producing well and an injection well and a dilution stream for enhancing oil recovery.

Referring now to FIG. 1, one embodiment of the present enhanced oil recovery method is shown. A hydrocarbon reservoir in a rock formation 170, is perfused with an injection water 160, whereby the injection water is supplied to the reservoir by an injection well 110. The injection water flows through the reservoir and intermingles with the formation water and extracts oil from the formation to create a produced water containing oil 150. This oil/water mixture flows out of the rock formation and back to the surface by a producing well 100. The produced water containing oil 150, is then transported to a processing station 120 where the oil is separated from the water. This separation step results in the oil product stream 130. The separation step also results in a produced water stream (not shown) that, in this embodiment, is altered with another water 140, which results in the injection water 160, which is now modified to optimize oil recovery from the rock formation.

Figure 2:
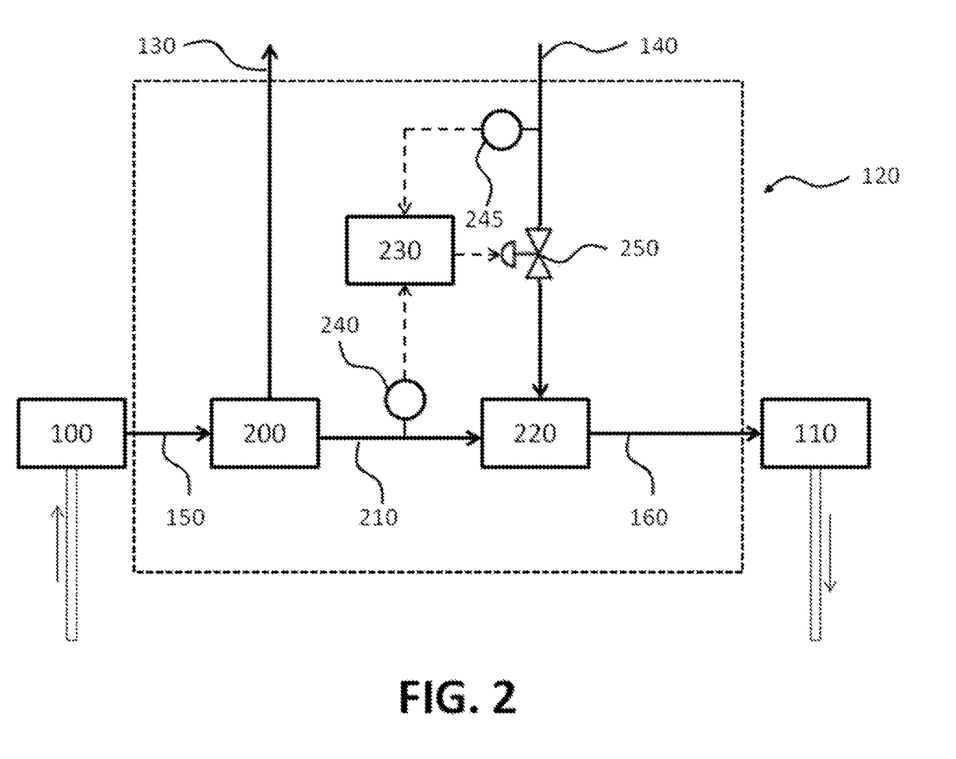
FIG. 2 illustrates one embodiment of the present invention, a block diagram of a processing station for adding a dilution water to a produced water to facilitate enhanced oil recovery.

Referring now to FIG. 2, one embodiment of a processing station 120 for producing a diluted injection water 160 is shown. The produced water containing oil 150 is transported to the surface of the producing well 100, where it is fed to an oil/water separator 200. This may be a gravimetric separator. The oil/water separator produces the oil product stream 130, and the produced water stream 210. At least one measurement device 240 analyzes the produced water stream. Metrics analyzed by the at least one measurement device may include, but are not limited to, pH, salinity, ion concentration, osmotic strength, flow rate, and temperature. These metrics are then communicated to a control center 230. The control center may comprise a computer system on which may be located at least one equilibrium model or algorithm. An alteration water stream 140 is also shown entering the processing station. This stream may also be analyzed by at least one measurement device 245. Like the at least one measurement device 240 for the produced water, the at least one measurement device for the alteration stream may measure metrics such as pH, salinity, ion concentration, osmotic strength, flow rate, and temperature. These alteration water metrics are also communicated to the control center 230. With both the produced water metrics and the alteration water metrics defined, the at least one equilibrium model or algorithm may then calculate at least one optimum target injection water 160 metric for optimizing oil recovery from the well. The control center may then target the at least on optimized injection water metric by controlling the flow of the alteration water 140, in this exemplary case, by manipulation of a control valve 250. The produced water and metered flow of alteration water are then mixed in a subsequent mixing station 220 to produce the actual injection water. A third at least one measurement device (not shown) may provide feedback control to the control center 230 to allow more accurate achievement of the optimum injection water target metric.

In some embodiments of the present invention, the method for increasing oil recovery may further comprise a modified flotation test. The objective of this test is to determine the natural condition of rock wetting at close to reservoir conditions and the effect of modifying the brine chemistry to establish if the modified brine will release additional oil from the rock. In some further embodiments of the present invention, the calculated alteration factor may be verified using reservoir rock and oil and produced water chemistry using the modified flotation test.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any sub-combination.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

Example 1—Correction to Analysis of Produced Water to More Accurately Estimate the Chemical Composition of the Reservoir Formation Water The following example utilizes Geochemist's Workbench and illustrates one method for adjusting the analysis of produced water to better estimate the chemical composition of the actual reservoir formation water. This in turn, will provide a more reliable optimized target metric for adjusting the produced water to create an injection water that is likely better suited to improve oil recovery, yield, etc.

In this particular example, the hypothetical formation is sandstone at 3 km depth and 100° C. The gas cap is 2% $CO_2$ and the reservoir rock contains quartz, calcite, K-feldspar and kaolinite. The formation water analysis is loaded into the Basis. Then the charge balance is set on Cl and quartz swapped for $SiO_2$. Next calcite is swapped for $HCO_3$ and the simulation run (Steps 1-3). The input file should look like the example below. Checking the calculated $PCO_2$ we find it is only about 10-5, much too low and the pH is unchanged. Assuming the reservoir is normally pressured, the reservoir pressure is about 298 bars and $CO_2$ in the gas cap is about 6 bars. Run React and slide the $CO_2$ to a fugacity of 6 (the slide command is under the Reactants tab). The pH is now 5.4 and the bicarbonate is 640 ppm. Note the system became super-saturated with respect to kaolinite, which precipitated. This matches well with the actual system.

We can now try the alternative approach of setting the pH by the feldspar-clay couple. Remove the $CO_2$ slide and swap K-feldspar for $H+$ and kaolinite for $Al+++$. The calculated pH is now 6.06 and the bicarbonate is 224. The $CO_2$ fugacity is now 0.48 bars, somewhat lower than the gas cap data.

In both cases the "corrected" analysis contains more bicarbonate than the original analysis (146 ppm) suggesting that $CaCO_3$ precipitated during production. To compensate for the loss of carbonate you can set the pH of the water analysis (corrected for temperature and silica) using the Fix command under the Reactants tab, remove the calcite swap and titrate calcite to reach equilibrium. Examine the React output file and you will see that for a pH of 5.4, equilibrium with calcite is reached when Ca is 1548 ppm and $HCO_3$ is 277 ppm. For a pH of 6.06, the Ca is 576 ppm and $HCO_3$ is 158 ppm at calcite equilibrium.

Given knowledge of the $CO_2$ content in the gas cap, we would choose the first case with the reservoir pH of 5.4. This corrected analysis could then be run with a reaction path that cooled the temperature and lowered the pH to the measured value in order to improve calculation of scaling potential.

Example 2—Modified Flotation Test

The first step is to establish a baseline condition by using reservoir oil, synthetic brine to mimic reservoir brine and reservoir rock.

Step 1—Crush and grind reservoir rock sample to fine powder. Prepare 0.2 gm aliquot for testing. [Note that amounts can be scaled to accommodate available material.]

Step 2—Age rock sample in 10 ml* of synthetic reservoir brine for 2 days at reservoir temperature.

Step 3—Decant brine and add 2-3 ml of reservoir oil to rock sample and age at reservoir temperature for 2 days. Agitate sample every 12 hours to ensure oil fully contacts rock powder.

Step 4—Add 10 ml synthetic brine to oil-rock mixture and stir. [Note that amounts can be scaled to accommodate available material.]

Step 5—Allow mixture to settle for 24 hours at reservoir temperature.

Step 6—Decant and separate floating rock powder from settled rock powder.

Step 7—Dry and weight rock powders from both settled and floating portions.

Repeat steps 1-7 substituting the modified brine in step 4 and compare with baseline.

For test below 110° C. the gas cap in the glass vials can be filled with specific gas mixtures to better emulate reservoir conditions. For temperatures above 110° C., tests can be performed with suitable high pressure vessels and live fluids to better match reservoir conditions.

The procedure can be repeated [0057] with adjusted "produced water" to further test and refine the optimum chemical composition.

APPENDIX

Chemical Equations
Surfaces

SurfA_OH=SurfA_O—+H+

SurfA_OH+H+=SurfA_OH2+

SurfB_OH=SurfB_O—+H+

SufA_OH+Ca2+=SurfA_OCa++H+

SufA_OH+Na+=SurfA_ONa+H+

SurfB_OH+Ca2+=SurfB_OCa++H+

SurfB_OH+Na+=SurfB_ONa+H+

SufA_OH+CaOH+=SurfA_OCaOH+H+

SurfB_OH=CaOH+=SurfB_OCaOH+H+

Ca_OH+H+=Ca_OH2+

Ca_OH+HCO3-=Ca_CO3—+H2O

Ca_OH2++SO42—=Ca_SO4+H2O

CO3_H=CO3_—+H+

CO3_H+Ca2+=CO3_Ca++H+

CO3_H+Mg2+=CO3_Mg++H+

Oil

Oil_COOH=Oil_COO—+H+

Oil_NH=Oil_N—+H+

Oil_NH2+=Oil_NH+H+

Oil_COO-+Ca2+=Oil_COOCa+

Surface+Oil

SufA_OH+Oil_COOCa+=SurfA_OCaCOO_Oil+H+

SufA_OH+OilNH2+=SufA_OHOilNH+H+

SurfB_OH+Oil_COOCa+=SurfB_OCaCOO_Oil+H+

SurfB_OH+OilNH2+=SurfB_OHOilNH+H+

SufA_OH2++Oil_COO-=SufA_OHOil_COO+H+

SurfB_OH2++Oil_COO-=SurfB_OHOil_COO+H+

Ca_OH2++OilCOO-=Ca_OHOilCOO+H+

Ca_OH+OilCOOH=Ca_OilCOO+H2O

CO3_H+OilNH2+=CO3_OilNH2+H+

CO3_—+OilNH+=CO3_OilNH

What is claimed is:

1. A method for increasing oil recovery from a subterranean hydrocarbon reservoir formation, comprising:
    recovering a produced water from the subterranean hydrocarbon reservoir formation and determining a salinity of the produced water;
    determining a natural condition of wettability in the subterranean hydrocarbon formation;
    treating the subterranean hydrocarbon reservoir formation to increase oil recovery by altering the produced water to create a treated produced water, wherein at least a first property of the treated produced water is based on the natural condition of wettability in the subterranean hydrocarbon formation; and
    injecting the treated produced water into the subterranean hydrocarbon reservoir formation, wherein the treated produced water interacts with the subterranean hydrocarbon reservoir formation to alter the natural condition of wettability in the subterranean hydrocarbon formation.

2. The method of claim 1, further comprising:
    altering the salinity of the produced water to create the treated water product.

3. The method of claim 2, wherein the altering the salinity of the produced water comprises the addition of a second water to the produced water from at least one of an aquifer, a river, a stream, a lake, an ocean, a subsurface formation, and combinations thereof.

4. The method of claim 3, wherein the second water further comprises inorganic salts.

5. The method of claim 3, wherein the second water further comprises at least one viscosifying polymer agent.

6. The method of claim 2, wherein the altering of the salinity comprises treating the produced water with at least one of a water softening process, a water deionization process, a water distillation process, and combinations thereof.

7. The method of claim 1, wherein the treated produced water interacts with the subterranean hydrocarbon reservoir formation to produce an increase in a pH in the subterranean hydrocarbon reservoir formation by about 0.75 pH units to about 2.0 pH units.

8. The method of claim 1, further comprising adjusting a pH of the produced water to account for changes due to loss of dissolved carbon dioxide during production to estimate the pH of the formation water chemistry in the subterranean hydrocarbon reservoir formation.

9. The method of claim 1, wherein a relative percentage of a carbonate mineral in the subterranean hydrocarbon reservoir rock is between about 2 wt. % and about 20 wt. %.

10. The method of claim 9, wherein the relative percentage of the carbonate mineral in an subterranean hydrocarbon reservoir rock is determined using an analysis method selected from the group consisting of an acid digestion, a geophysical log, a thin section point counting, a well cuttings analysis, and X-ray diffraction.

11. The method of claim 1, wherein a relative percentage of a sulfate mineral in the subterranean hydrocarbon reservoir rock is between about 0.5 wt. % and about 5 wt. %.

12. The method of claim 11, wherein the sulfate mineral comprises at least one of gypsum, anhydrite, and combinations thereof.

13. The method of claim 1, wherein a relative percentage of a clay mineral in the subterranean hydrocarbon reservoir rock is between about 2 wt. % and about 20 wt. %.

14. The method of claim 1, wherein a salinity of the produced water is altered by an addition of an acid, a base, a salt and combinations thereof.

15. The method of claim 1, wherein the produced water is altered by an addition of a density modifier, a pH adjustment agent, a salinity adjustment agent, a displacement agent, a dispersant and combinations thereof.

16. The method of claim 1, wherein the subterranean hydrocarbon reservoir rock comprises at least one of a sandstone, a limestone, a dolomite, and a chalk.

17. The method of claim 1, wherein the injecting of the treated produced water into the subterranean hydrocarbon formation reservoir is repeated at least one additional cycle.

18. The method of claim 1 further comprising:
   testing the treated produced water to determine a modified condition of water wettability based on the treated produced water.

19. The method of claim 18, wherein the testing is repeated with different treated produced water to determine an optimum chemical composition of the treated produced water.

20. The method of claim 18, wherein the injecting comprises modifying the natural condition of the wettability in the subterranean hydrocarbon formation to the modified condition of wettability in the subterranean hydrocarbon formation in order to increase recovery.

* * * * *